(12) United States Patent
Su et al.

(10) Patent No.: US 10,688,343 B2
(45) Date of Patent: Jun. 23, 2020

(54) MEASURING METHOD FOR MAXIMUM MUSCLE STRENGTH

(71) Applicant: Strength Master Fitness Tech. Co., Ltd., Puxin Township (TW)

(72) Inventors: Ming-Chu Su, Puxin Township (TW); Shu-Yao Wu, Puxin Township (TW); Pei-Hsuan Chang, Puxin Township (TW)

(73) Assignee: Strength Master Fitness Tech. Co., Ltd., Puxin Township (TW)

( * ) Notice: Subject to any disclaimer, the term of this patent is extended or adjusted under 35 U.S.C. 154(b) by 347 days.

(21) Appl. No.: 15/783,786

(22) Filed: Oct. 13, 2017

(65) Prior Publication Data
US 2019/0111316 A1 Apr. 18, 2019

(51) Int. Cl.
| | | |
|---|---|---|
| *A63B 24/00* | (2006.01) |
| *A61B 5/22* | (2006.01) |
| *A63B 21/00* | (2006.01) |
| *A63B 21/06* | (2006.01) |
| *A63B 22/00* | (2006.01) |
| *A61B 5/11* | (2006.01) |

(52) U.S. Cl.
CPC .......... *A63B 24/0062* (2013.01); *A61B 5/224* (2013.01); *A63B 21/4043* (2015.10); *A61B 5/11* (2013.01); *A63B 21/06* (2013.01); *A63B 21/151* (2013.01); *A63B 21/156* (2013.01); *A63B 21/4033* (2015.10); *A63B 21/4035* (2015.10); *A63B 22/0087* (2013.01); *A63B 2022/0035* (2013.01); *A63B 2022/0079* (2013.01); *A63B 2024/0065* (2013.01); *A63B 2220/17* (2013.01); *A63B 2220/51* (2013.01); *A63B 2220/803* (2013.01); *A63B 2220/808* (2013.01)

(58) Field of Classification Search
CPC ........ A63B 24/0062; A63B 2024/0065; A63B 21/151; A63B 21/4033; A63B 21/06; A63B 24/0065
USPC .......... 73/379.01–379.01; 700/90; 702/1, 19, 702/33, 41, 44, 127, 173, 175, 182; 482/92–139
See application file for complete search history.

(56) References Cited

U.S. PATENT DOCUMENTS

| | | | | |
|---|---|---|---|---|
| 5,452,727 A | * | 9/1995 | Tura ........................ | A61B 5/224 128/860 |
| 2014/0128784 A1 | * | 5/2014 | Wiley ................ | A63B 71/0622 601/40 |

* cited by examiner

*Primary Examiner* — Robert R Raevis
(74) *Attorney, Agent, or Firm* — Wang Law Firm, Inc.

(57) ABSTRACT

A measuring method for maximum muscle strength may be applied to a muscle training device and a user of the device. The muscle training device may include a control unit, an operation display unit, and a drag unit. The measuring method assists the user to measure their maximum strength on the muscle training device by themselves, and this knowledge is helpful in designing and adjusting a muscle training schedule and to evaluate the resulting progress.

10 Claims, 8 Drawing Sheets

MEASURING METHOD FOR MAXIMUM MUSCLE STRENGTH

BACKGROUND OF THE INVENTION

1. Field of the Invention

The present invention relates to a measuring method. Particularly, the present invention relates to a maximum muscle strength measuring method used on a muscle training device.

2. Description of the Related Art

Maximum muscle strength is the maximum tension that can be generated in one maximal contraction when overcoming an opposite force, where such an opposing force is termed herein a resistance to the muscle generated tension. In practice, the maximum muscle strength is equal to the muscle strength of 1 RM (one-repeat maximum), which is the maximum force generated in one contraction of a muscle or the maximum muscle strength generated in one contraction of a group of muscles against the opposing pulling force due to some weight. Therefore, for practical purposes, the unit of measurement for 1 RM is kilograms of weight. For example, a person may only push once in a chest press, and the resultant chest press 1 RM of the person is 70 kg. In other words, his maximum muscle strength is 70 kg.

The 1 RM test can be helpful in the design of training schedules or in evaluating training progress. It may also help understand changes in the balance between the person's agonist and antagonist muscles.

There are two conventional methods for evaluating 1 RM: estimation and direct measurement. The estimation method is suitable for a person who is not yet familiar with the exercise procedures in their prescribed or chosen training regime, e.g. in weight training. The calculation of 1 RM involves multiplying the setup weight by the coefficient corresponding to the maximum count. As for the direct measurement method, the person first performs the exercise with 3 different weights to determine the attainable 1 RM resistance for that person. If the 1 RM resistance due to the heaviest weight tested is overcome, the person gets a rest and is then challenged with resistances increasing by a weight in the range 5 lb to 10 lb. If the person fails to overcome a resistance, they also get a rest and are then challenged to resistances decreasing by a weight also in the range of 5 lb to 10 lb. The procedure is repeated until the 1 RM muscle strength is approached.

Although muscle training devices are commonly used today, 1 RM is still acquired by manual calculation and may be provided by professionals such as a gym personal fitness trainer. However, this may be inconvenient for people following a muscle training regime, for example, personal training clients.

Therefore, it would be useful to be able to evaluate one's own 1 RM or maximum muscle strength by oneself without extra expert or professional assistance, by simply using a muscle training device.

SUMMARY OF THE INVENTION

For the aforementioned purpose, the present invention provides a maximum muscle strength measuring method, which is applicable to a muscle training device, the device including a drag unit, an operation display unit, and a control unit, the method comprising the steps of:

a. Selecting a muscle of the user or a motion to be measured, for which maximum muscle strength will be measured, through the operation display unit;

b. Setting up a resistance value through the display unit and generating one or more test resistance values based on different proportions of the resistance value;

c. Generating at least one drag force based on at least one test resistance value;

d. Overcoming at least one drag force by the user moving or steadily holding the drag unit, and measuring a moving distance or a steady operation time of the drag unit for completing the motion by a position sensor and the control unit;

e. Judging whether the moving distance or the steady operation time of the drag unit meets a condition for generating a muscle strength value or not, wherein the condition for generating the muscle strength value includes the moving distance or the steady operation time of the drag unit;

f. Obtaining a maximum muscle strength coefficient based on an accumulative number of times that the user meets the condition for generating the muscle strength value continuously in the step e, and calculating the muscle strength value via dividing the resistance value by the maximum muscle strength coefficient;

g. Generating a corresponding test drag force for the drag unit based on the muscle strength value;

h. Lowering the muscle strength value by a lowering proportion if the user is unable to overcome the test drag force and meet the condition for generating the muscle strength value, and returning to step g;

i. Raising the muscle strength value by a raising proportion and returning back to step g if the user continuously overcomes the test drag force to complete more than one time of a measurement of step e and meets the condition for generating the muscle strength value;

j. Outputting the muscle strength value as the maximum muscle strength if the user is able to overcome the test drag force and meet the condition for generating the muscle strength value only once.

The condition for generating the muscle strength value may be adjusted to a certain proportion of the moving distance or the steady operation time of the drag unit.

The condition for generating the muscle strength value based on the moving distance or the steady operation time may be set or inputted through the operation display unit.

A start position and a final position or a start time and an end time for the condition for generating the muscle strength value may be inputted through the operation display unit.

The condition for generating the muscle strength value may be set and inputted into the operation display unit by means of a sound or motion sensor.

Preferably, the moving distance or the steady operation time is the average of a number of moving distances or of steady operation times in which the user has overcome the drag force or the test drag force at least once to move the drag unit as in step (d).

For the aforementioned purpose, the present invention also provides another maximum muscle strength measuring method, which is applicable to a user and a muscle training device, the device including a drag unit, an operation display unit, and a control unit, the method comprising the steps of:

a. Selecting a muscle of the user or a motion to be measured through the operation display unit;

b. Setting up a resistance value through the operation display unit, and generating a test resistance value by the control unit, and generating a test drag force for the drag unit based on the test resistance value;

c. Overcoming the test drag force by the user moving or steadily holding the drag unit;

d. Judging by the control unit whether the moving distance or the steady operation time of the drag unit meets the condition for generating a muscle strength value of not, wherein the condition for generating the muscle strength value is based on the moving distance or the steady operation time of the drag unit, and determining the moving distance and the steady operation time of the drag unit for completing the measurement by a position sensor and the control unit;

e. Counting an accumulative number of times of completing the measurement in the step d until a preset number of times is reached;

f. Obtaining a maximum muscle strength coefficient based on the accumulative number of times, and calculating the maximum muscle strength by multiplying the resistance value by the maximum muscle strength coefficient.

The condition for generating the muscle strength value may be adjusted to a certain proportion of the moving distance or the steady operation time of the drag unit.

The condition for generating the muscle strength value corresponding to the moving distance or the steady operation time may be set or inputted through the operation display unit.

A start position and a final position or a start time and an end time for the moving distance or the steady operation time may be inputted through the operation display unit.

The condition for generating the muscle strength value may be set and inputted into the operation display unit by means of a sound or motion sensor.

DESCRIPTION OF THE PREFERRED EMBODIMENTS

Figure 1:
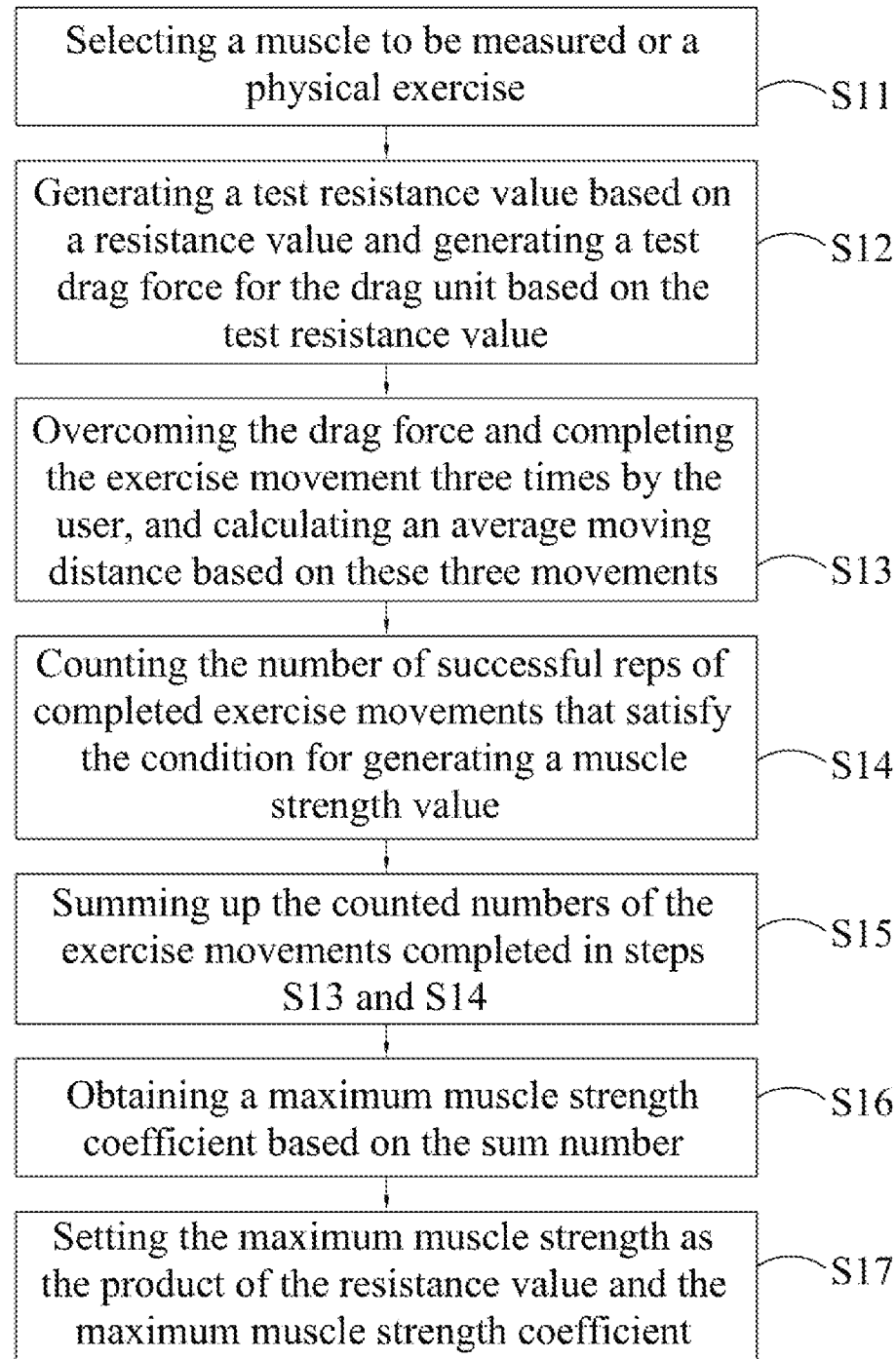
FIG. 1 is a first flow chart showing an embodiment of the maximum muscle strength measuring method of the present invention.
Figure 2:
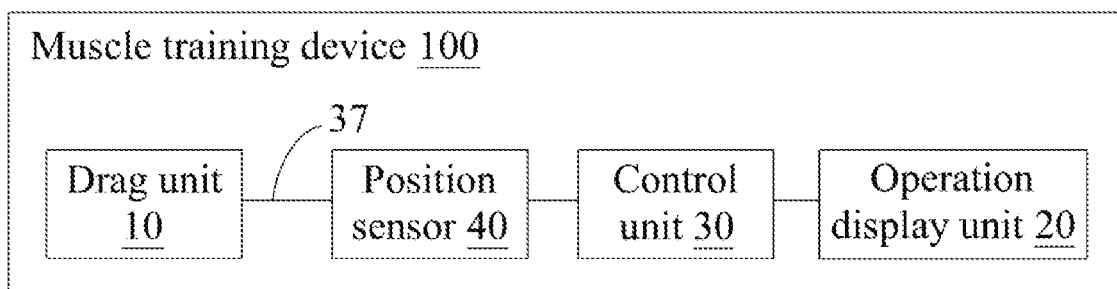
FIG. 2 is a system block diagram for an embodiment of the maximum muscle strength measuring method of the present invention.

The technical features, content, advantages and effects of the present invention will be presented hereinafter through embodiments accompanied with corresponding figures. The figures are only for the purpose of illustration and example, and do not necessarily imply the actual dimensions or precise configuration of the possible implementations of the present invention. Therefore, the present invention should not be considered as limited by the dimensions or configuration shown in the figures.

Referring to FIGS. 1-6, which are a first flow chart showing an embodiment of the maximum muscle strength measuring method, a system block diagram for an embodiment of the maximum muscle strength measuring method, a second flow chart applying to a muscle training device, a first, second and third schematic diagrams each showing a muscle training device of the present invention. The maximum muscle strength measuring method may be applied on a user 90 and a muscle training device 100 including a drag unit 10, an operation display unit 20, and a control unit 30.

The operation display unit 20 may receive a command inputted by the user 90 and transfer the command to the control unit 30. The control unit 30 may perform a calculation based on the command and control the pulling unit 10 to increase or to decrease its resistance. The control unit 30 may also provide an output prompt message on the operation display unit 20.

The operation display unit 20 may include a touch screen, a software program, a motion sensor or a sound sensor. The control unit 30 may include a processor capable of performing calculations. The drag unit 10 may include a drag assembly for muscle training. A position sensor 40 may be included to detect the movement of the drag unit 10 and to record its initial and final positions.

In embodiments of the present invention, the maximum muscle strength measuring method and muscle training device 100 may respectively include process steps and components that may be implemented using various types of operating systems and/or computer programs, and the components may include devices designed for a specific purpose, such as hardwired devices, field programmable gate arrays (FPGAs), application specific integrated circuits (ASICs), or the like. Furthermore, the components, that may include such computing devices, may include a central processing unit, memory (e.g. ROM, PROM, EEPROM, flash memory, and others), input devices (e.g. a touchscreen), and output devices (e.g. a display), and removal storage capability (e.g. a USB flash drive port). The memory and storage devices are computer-readable media that may be encoded with computer-executable instructions. Such implementations may be used without departing from the scope and spirit of the inventive concepts disclosed herein.

Figure 4:
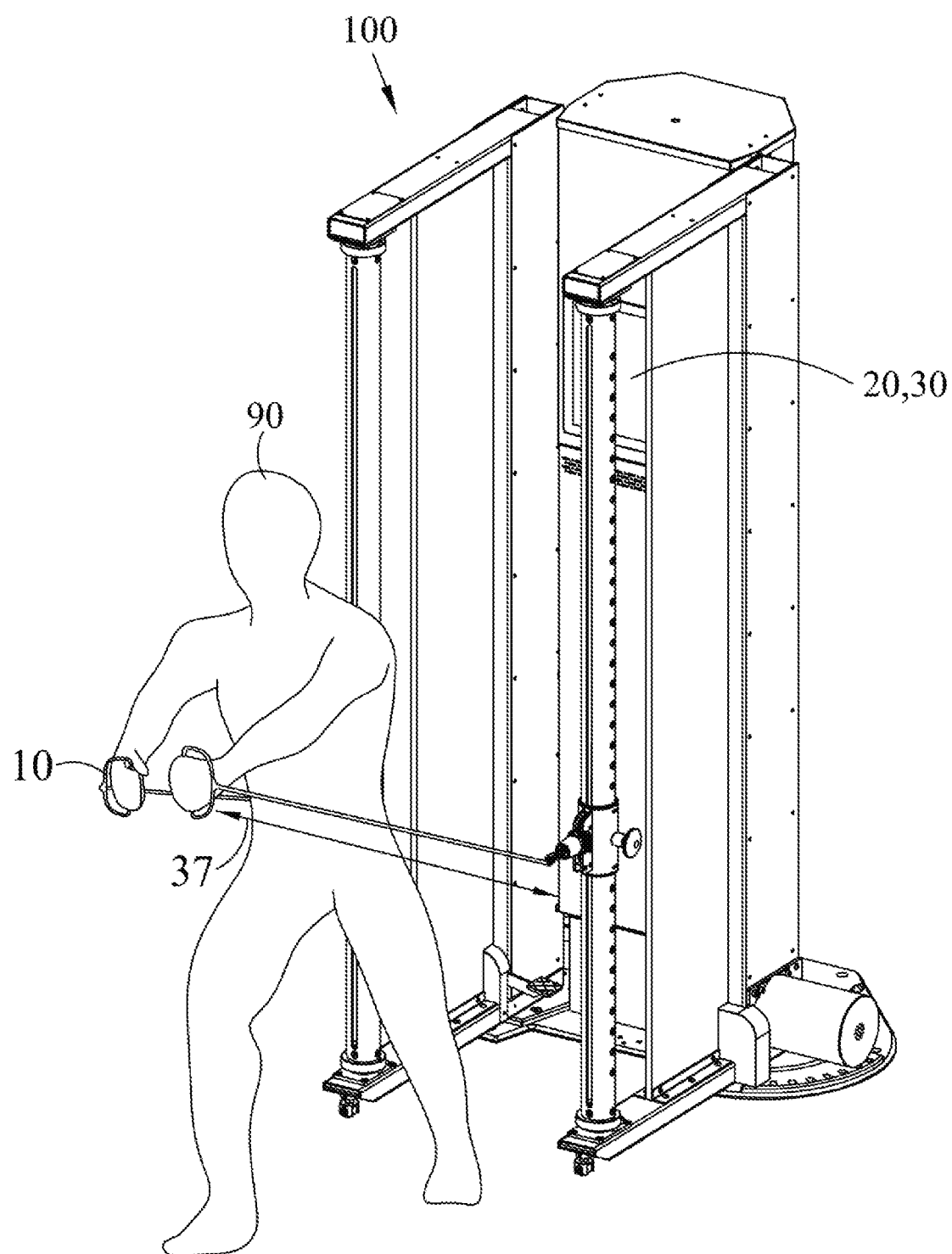
FIG. 4 is a first schematic diagram showing a muscle training device of the present invention
Figure 5:
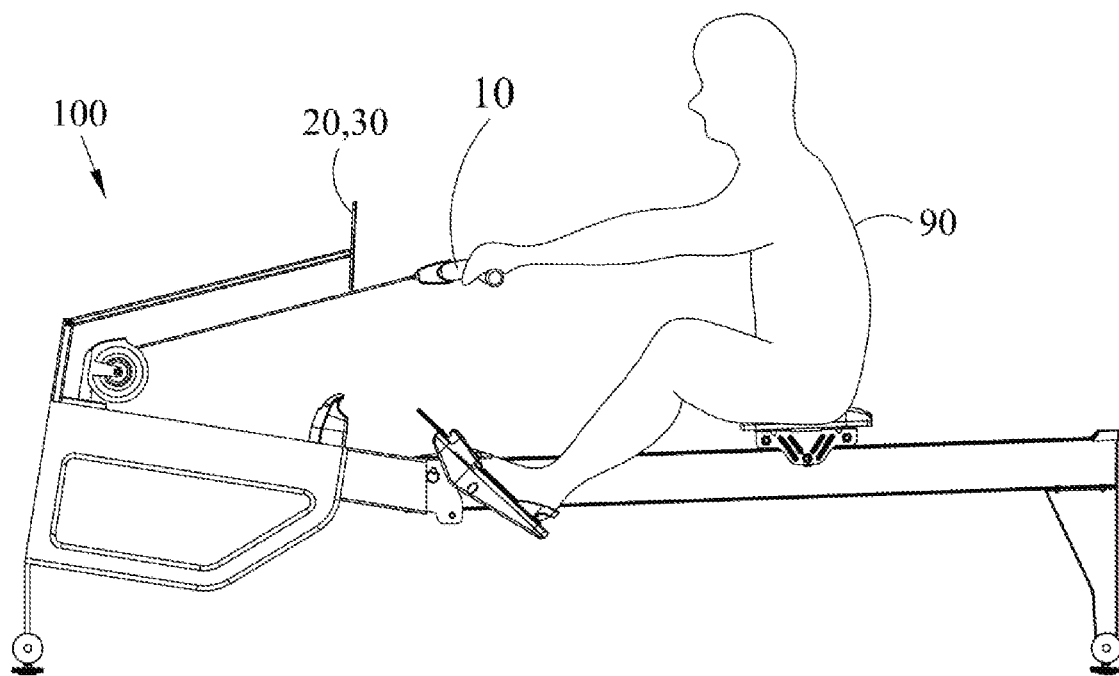
FIG. 5 is a second schematic diagram showing a muscle training device of the present invention.
Figure 6:
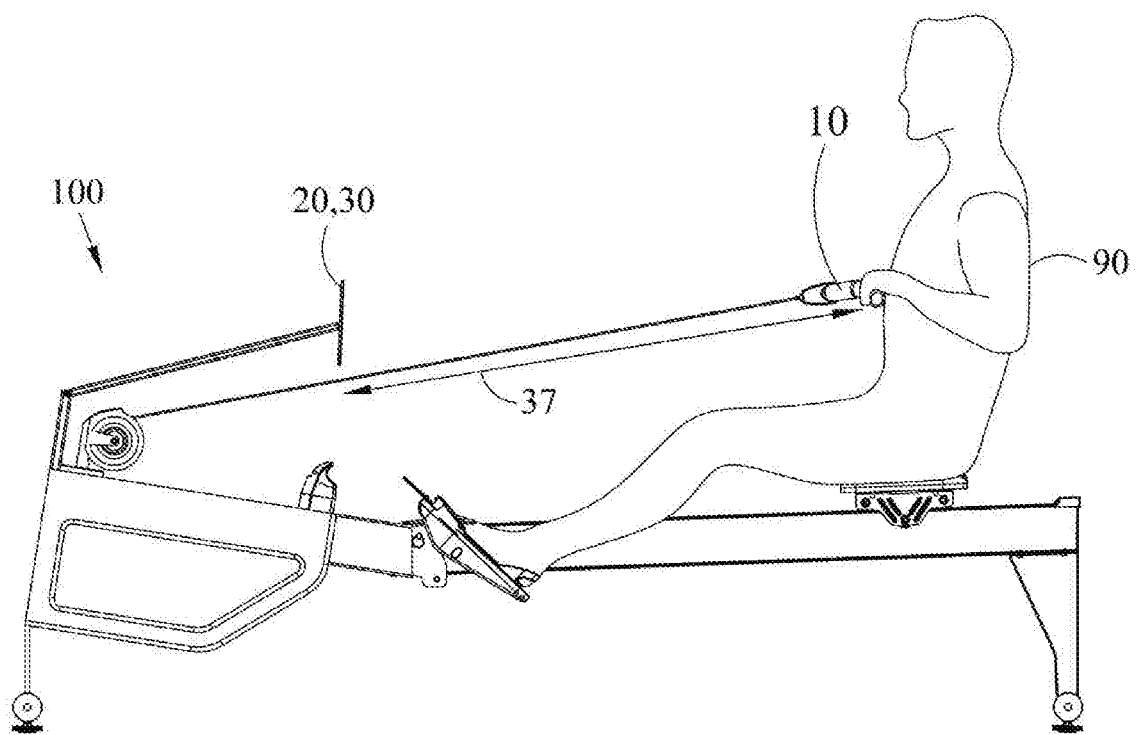
FIG. 6 is a third schematic diagram showing a muscle training device of the present invention.

The muscle training device 100 in this embodiment may be, but is not limited to, a rowing muscle training device as shown in FIG. 5 or a multi-functional dual pulley training device shown in FIG. 4. A typical rowing muscle training device can help build a user's latissimi dorsi muscles and can measure the maximum pulling strength of the muscles. The multi-functional dual pulley training device provides for a user to perform the chest fly or chest press exercises and help build the pectoralis major muscles and can measure the muscles' maximum pushing strength for the muscles. The multi-functional dual pulley training device can also help a user to perform the inverted fly or other pulling exercises for the back and may, therefore, be used to measure maximum pulling strength for the muscles used.

Muscle performance can be measured through these pushing and pulling exercises and knowing their muscle performance, enables the user 90 to understand and track their muscles' performance. The maximum muscle strength can be measured by the method and includes the following steps:

A step S11 of selecting a muscle to be measured of a user 90 and/or selecting a physical exercise through the operation display unit 20.

A step S12 of generating a test resistance value based on a resistance value by the control unit 30 and generating a test drag force, for the drag unit 10 to exert or resist, based on the test resistance value, wherein the resistance value may be an arbitrary value inputted by the user 90. The preferred resistance value is the maximum muscle strength assumed by the user 90.

A step S13 of overcoming the drag force and completing three cycles of the exercise movement by the user 90, and calculating an average moving distance based on the three cycles.

A step S14 of counting the number of continuous successful repetitions (reps), where a successful rep is a complete cycle of motion of the exercise, away from and back to a fixed starting point, that meets a predefined condition in order to be counted towards a muscle strength value, wherein the condition includes an operation time less than a preset operation time of 5 seconds or an operation moving distance greater than or equal to 80% of the average moving distance, wherein the preset operation time or the operation moving distance is acquired on completion of the exercise movement, that is a cycle or rep of the exercise.

A step S15 of summing up the counted numbers of the exercise movements completed in steps S13 and S14 by the control unit 30.

From the fourth exercise movement, an exercise movement is counted only if the condition for generating a muscle strength value is satisfied, which means if the condition is not satisfied at the nth time, then the counting number is n−1.

A step S16 of looking up a maximum muscle strength coefficient based on the sum number of step S15 by the control unit 30. The corresponding maximum muscle strength coefficients are listed in the table below. For example, the muscle training device 100 is used to evaluate upper muscles such as the chest muscles or the arm muscles. If the user 90 has a counting number of 8, the corresponding muscle strength coefficient is 1.255.

| 1 RM maximum muscle strength coefficient | | |
| --- | --- | --- |
| Number of repetitions completed | Squat or leg press coefficient | Bench or chest press coefficient |
| 1 | 1.000 | 1.000 |
| 2 | 1.0475 | 1.035 |
| 3 | 1.13 | 1.08 |
| 4 | 1.1575 | 1.115 |
| 5 | 1.2 | 1.15 |
| 6 | 1.242 | 1.18 |
| 7 | 1.284 | 1.22 |
| 8 | 1.326 | 1.255 |
| 9 | 1.368 | 1.29 |
| 10 | 1.41 | 1.325 |

A step S17 of setting the maximum muscle strength as the product of the resistance value and the maximum muscle strength coefficient by the control unit 30. As in the example of step S16, if the initial muscle strength is 50 kg and the user 90 has a counting number of 8, the maximum muscle strength is 50 multiplied by 1.255. If the user 90 has a counting number of 1, the maximum muscle strength is 50 kg. In this approach, the present invention provides a method to estimate or measure the maximum muscle strength of the user 90.

In an embodiment, step S17 may optionally include re-assigning the acquired maximum muscle strength to be the resistance value through the operation display unit 20 and repeating step S12. For example, on the operation display unit 20, the user 90 may set up a desired number of rounds to be executed. If the number of rounds is 3, the sequence from S12 to S17 will then be executed 3 times. The repetition can help to find a better approximation to the user 90's maximum muscle strength.

In an alternative embodiment, the user 90 inputs a preset shift value 37 associated with the drag unit 10 on the operation display unit 20 in step S13 to step S14. The preset shift value 37 is used to evaluate the moving distance of the drag unit 10. When the moving distance of drag unit 10 driven by muscles is longer than, equal to, or close to the preset shift value 37, the control unit 30 considers the muscle exercise movement to be completed.

In an alternative embodiment for step S13 to S14, a start position and a final position of the drag unit 10 are set up through the operation display unit 20 to define a preset shift value 37. When the moving distance of drag unit 10 driven by muscles is longer than, equal to, or close to the preset shift value 37, the control unit 30 considers the muscle test movement to be completed.

In an embodiment, the measuring method of the present invention may further include automatically or manually increasing the resistance value when the counting number is greater than 10 and going back to step S11. As explained above, the maximum muscle strength is the maximum amount of force that can be generated in one contraction by one single muscle. If the counting number is greater than 10, the resistance value as the measured strength is considered easy for the user 90. The resistance value, in this case, is not likely to be the real maximum muscle strength of the user 90. Therefore, in order to find the real maximum muscle strength, the resistance value needs to be increased and the measuring method of the present invention repeated.

Figure 3:
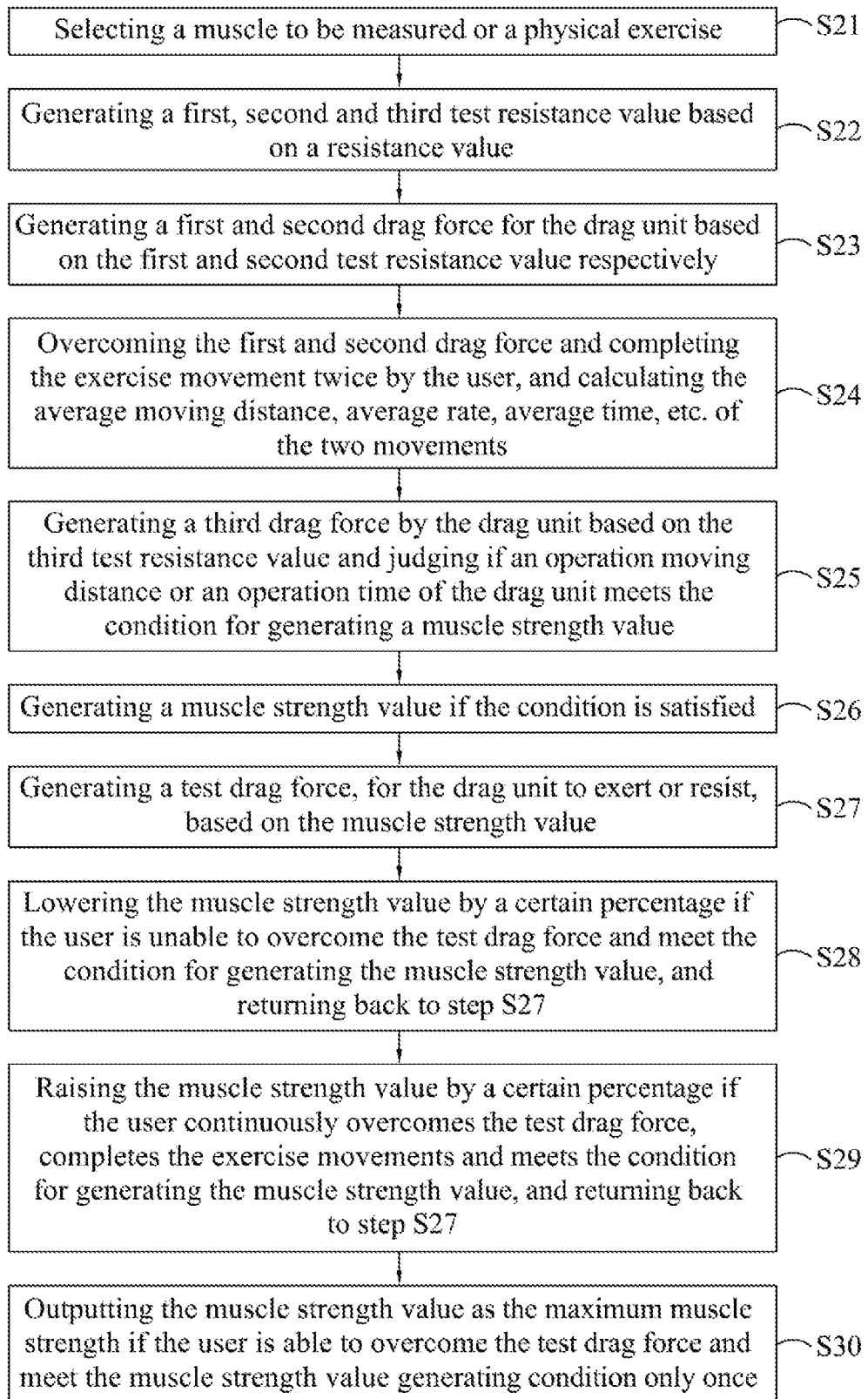
FIG. 3 is a second flow chart applying to a muscle training device of the present invention.

Referring to FIGS. 3 and 4, which are a second flow chart and first schematic diagram showing an example of how the maximum muscle strength measuring method of the present invention applies to the user 90 and the muscle training device 100. The muscle training device 100 includes the drag unit 10, the operation display unit 20, and the control unit 30, all of which are equivalent to those detailed in the previous embodiments.

The measuring method of the present embodiment may include the following steps:

A step S21 of selecting a muscle of a user 90 to be measured or a physical exercise through the operation display unit 20.

A step S22 of generating a first test resistance value, a second test resistance value, and a third test resistance value based on a resistance value. The resistance value may be the maximum muscle strength assumed by the user 90. The first test resistance value, the second test resistance value, and the third test resistance value may respectively be 50%, 70%, and 85% of the resistance value.

A step S23 of generating a first drag force and a second drag force, for the drag unit 10 to exert or resist, based respectively on the first test resistance value and the second test resistance value.

A step S24 of overcoming the first drag force and the second drag force and completing the exercise movement by the user 90, and completing the exercise movements twice and calculating the average moving distance, average rate, average time, etc. of the two movements.

A step S25 of generating a third drag force for the drag unit 10 based on the third test resistance value and judging if an operation moving distance or an operation time of the drag unit 10 meets the condition for generating a muscle strength value. The condition may include reaching a proportional value of the average moving distance or finishing within the preset operation time. For example, the condition for generating a muscle strength value may be the operation moving distance being greater than or equal to 80% of the average moving distance or the operation time being less than or equal to the preset operation time, which is 5 seconds in this case.

A step S26 of generating a muscle strength value if the condition is satisfied, wherein the muscle strength value is equal to the resistance value divided by a maximum muscle strength coefficient listed in the table below. In this embodiment, if the user 90 is able to meet the condition for generating the muscle strength value and complete the exercise movement three times, the maximum muscle strength coefficient corresponding to 3 times (3 exercise cycles) is 93% as shown in the table. Therefore, if the setup resistance value is 100 kg, the muscle strength value is equal to 100 divided by 0.93, which will be the starting resistance value for step S27.

| Repetitions | % 1 RM |
| --- | --- |
| 1 | 100 |
| 2 | 95 |
| 3 | 93 |
| 4 | 90 |
| 5 | 87 |
| 6 | 85 |
| 7 | 83 |
| 8 | 80 |
| 9 | 77 |
| 10 | 75 |
| 11 | 70 |
| 12 | 67 |
| 15 | 65 |

A step S27 of generating a test drag force for the drag unit 10 by the control unit 30 based on the muscle strength value.

A step 28 of lowering the muscle strength value by a certain percentage if the user 90 cannot overcome the test drag force and meet the condition for generating the muscle strength value, and returning back to step S27.

A step S29 of raising the muscle strength value by a certain percentage if the user 90 continuously overcomes the test drag force, completes the exercise movements and meets the condition for generating the muscle strength value, and returning back to step S27.

A step S30 of outputting the muscle strength value as the maximum muscle strength if the user 90 is able to overcome the test drag force and meet the muscle strength value generating condition only once.

In steps S28 and S29, if the muscle measured is of the upper body, the percentage change (lower or higher) may be around 2.5% to 5%, and if the muscle is of the lower body, the percentage change (lower or higher) may be around 5% to 10%.

In a preferred embodiment, the present measuring method may further include optionally setting the muscle strength value as the resistance value after step S30 and repeating the procedure from step S22 in order to attain a more accurate value for the maximum muscle strength.

In another embodiment, step S26 may further include lowering the resistance value if the condition for generating the muscle strength value is not satisfied and executing step S22, wherein the resistance value may be reduced by between 2 kg to 3 kg. In a preferred embodiment, the resistance value is reduced by 2.5 kg.

In another embodiment, in steps S24 and S25, a start position and a final position of the drag unit 10 are set through the operation display unit 20 to define a preset shift value 37. When the moving distance of drag unit 10 is greater than the preset shift value 37 or the drag unit 10 is steadily held for a period of time, the control unit 30 considers the muscle test movement to be completed.

When the drag unit 10 is moved further than the preset shift value 37, the muscle is in concentric contraction or eccentric contraction. When the drag unit 10 is steadily held for a period of time, the muscle is in isometric contraction.

In an embodiment, in steps S24 and S25, the user 90 inputs a start position and a final position for the drag unit 10 through the operation display unit 20 to define the preset shift value 37. The preset shift value 37 is used to evaluate the moving distance of the drag unit 10. When the moving distance of the drag unit 10 exceeds the preset shift value 37, the control unit 30 considers the test of the first drag force and the second drag force to be completed. When the third drag force is generated for the drag unit 10 based on the third test resistance value, the moving distance of the drag unit 10 is evaluated. If it reaches the preset shift value 37, the condition for generating a muscle strength value is satisfied.

In an embodiment, in addition to a touchscreen, sensors such as a sound or motion sensor may also be used to assist the user 90 in inputting the settings through the operation display unit 20.

In an embodiment, the threshold for a successful rep corresponding to the moving distance or the steady operation time is set or inputted through the operation display unit 20.

Figure 7:
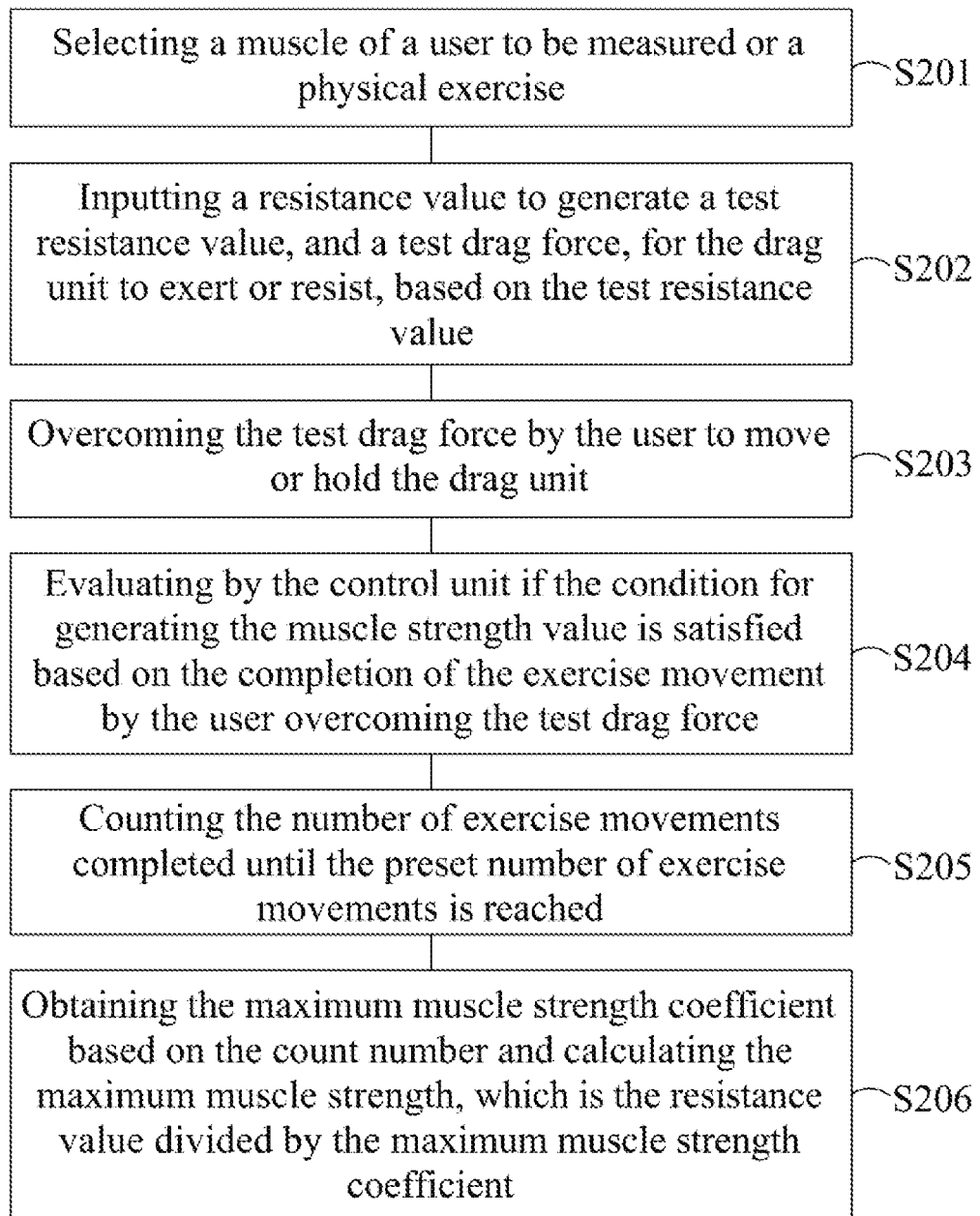
FIG. 7 is a third flow chart showing an embodiment of the maximum muscle strength measuring method of the present invention.

Referring to FIG. 7, which is the third flow chart showing an embodiment of the maximum muscle strength measuring method of the present invention. In an embodiment, a position sensor 40 is used to determine the moving distance of the drag unit 10 in a completed exercise movement or to determine the duration of the steady operation time. The method includes the steps of:

A step S201 of selecting a muscle of a user 90 to be measured or a physical exercise through the operation display unit 20.

A step S202 of inputting a resistance value through the operation display unit 20 to generate a test resistance value, and a test drag force, for the drag unit 10 to exert or resist, based on the test resistance value.

A step S203 of overcoming the test drag force by the user 90 to move or hold the drag unit 10.

A step S204 of evaluating by the control unit 30 if the condition for generating the muscle strength value is satisfied based on the completion of the exercise movement by the user overcoming the test drag force, wherein the threshold is the preset shift value 37 or the preset operation time of the drag unit 10, and the moving distance or the steady operation time of the completed exercise movement is generated by the position sensor 40.

A step S205 of summing up the counting numbers of the exercise movements completed in steps S203 and S204 until the preset number of exercise movements is reached.

A step S206 of obtaining the maximum muscle strength coefficient based on the cumulative number and calculating the maximum muscle strength, which is the resistance value divided by the maximum muscle strength coefficient.

Figure 8:
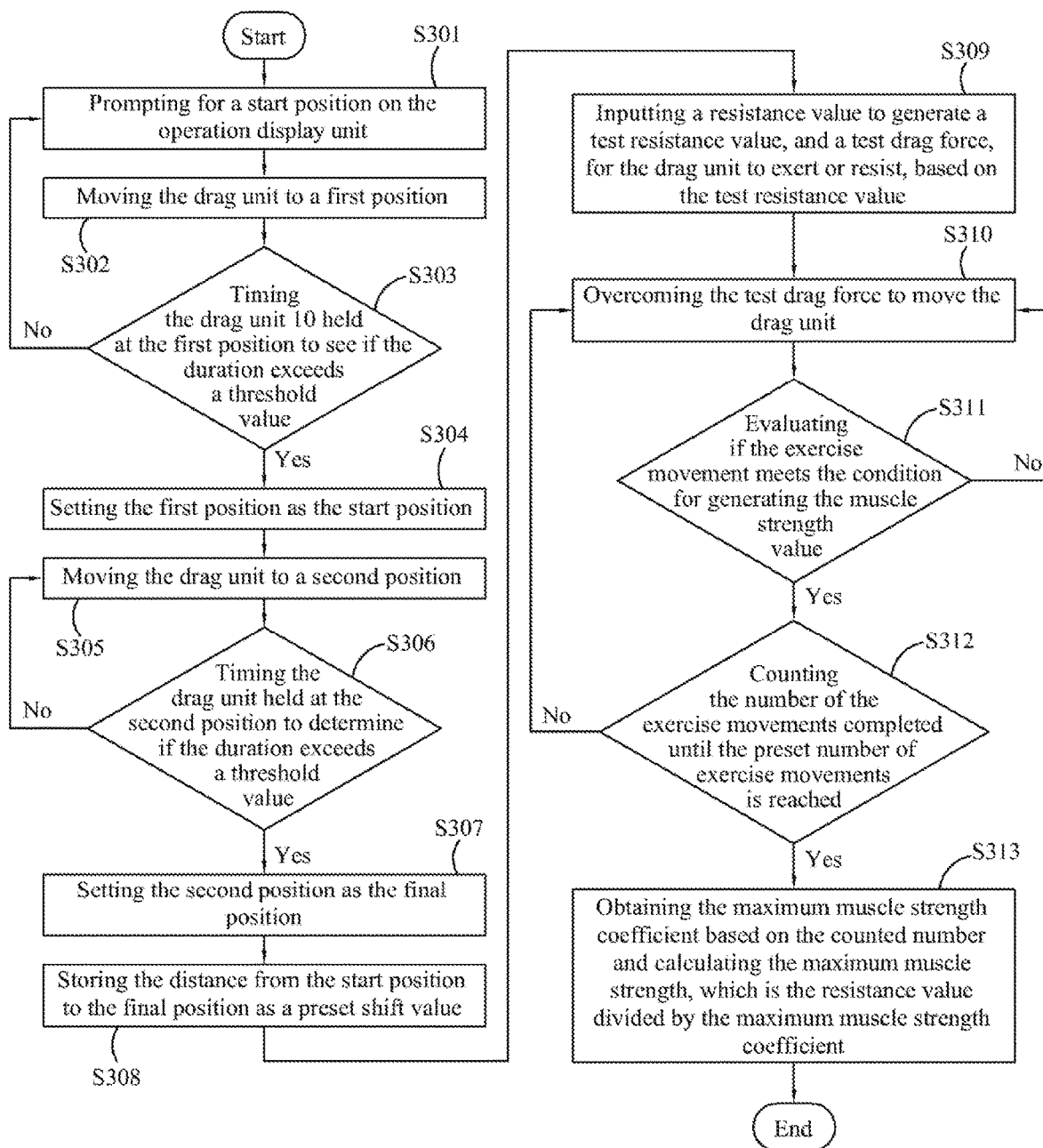
FIG. 8 is a fourth flow chart showing an embodiment of the maximum muscle strength measuring method of the present invention.

In an embodiment, the operation display unit 20 may prompt the user 90 to input a start position and a final position of the drag unit 10 in order to set a preset shift value 37. When the moving distance of the drag unit 10 exceeds the preset shift value 37, the control unit 30 considers the exercise movement to be completed. The setting of the preset shift value 37 and the measurement of the maximum muscle strength are shown in FIG. 8, which is the fourth flow chart showing an embodiment of the maximum muscle strength measuring method the present invention.

A step S301 of prompting for a start position on the operation display unit 20.

A step S302 of moving the drag unit 10 to a first position by the user 90.

A step S303 of timing the drag unit 10 held at the first position to see if the duration exceeds a threshold value.

A step S304 of setting the first position as the start position if the duration exceeds the threshold value, or otherwise returning back to step S301.

A step S305 of continuously moving the drag unit 10 to a second position.

A step S306 of timing the drag unit 10 held at the second position to determine if the duration exceeds a threshold value.

A step S307 of setting the second position as the final position if the duration exceeds the threshold value, or returning back to S306.

A step S308 of recording the distance between the start position and the final position as a preset shift value 37 by the control unit 30.

A step S309 of inputting a resistance value on the operation display unit 20 to generate a test resistance value, and generate a test drag force, for the drag unit 10 to exert or resist, based on the test resistance value.

A step S310 of overcoming the test drag force to move the drag unit 10 by the user 90.

A step S311 of evaluating by the control unit 30 if the condition for generating the muscle strength value is satisfied based on the completion of the exercise movement by the user overcoming the test drag force, wherein the condition is the drag unit 10 reaching the final position and the completion of the exercise movement.

A step S312 of summing up the counting numbers of the exercise movements completed in steps S310 and S311 until the preset number of exercise movements is reached.

A step S313 of obtaining the maximum muscle strength coefficient based on the sum number and calculating the maximum muscle strength, which is the resistance value divided by the maximum muscle strength coefficient.

In this embodiment, when the user 90 does not move the drag unit 10 to the final position and complete the exercise movement, the user 90 may optionally execute step S310 and attempt to move the drag unit 10 again or step S313 to directly calculate the maximum muscle strength.

In step S312, the preset number of exercise movements may be set as 1. In this case, the maximum muscle strength of the user 90 is directly measured. Calculating the maximum muscle strength, by dividing the resistance value by the maximum muscle strength coefficient, is then unnecessary.

In an embodiment, a start position and a final position or a start time and an end time may be inputted through the operation display unit 20 for the moving distance or the steady operation time of a successful rep.

In step S309, sensors such as a sound or motion sensor may also be used to assist the user 90 in inputting settings through the operation display unit 20.

As explained above, when the counting number is greater than 10, the measured strength corresponding to the resistance value is considered easy for the user 90. The resistance value, in this case, is not likely to be the real maximum muscle strength. Therefore, the preset number of exercise movements of less than 10 used in the present invention is reasonable to acquire a credible value for the maximum muscle strength. If the counting number 10 is easily reached, the resistance value is too low for the user 90. In this case, go to step S309 and input a more reasonable resistance value.

The preset number of exercise movements can be manually set or may already be preset in the muscle training device 100 by default. If the preset number of exercise movements is 10 and the user 90 is able to finish the movement more than 10 times, the resistance value is then too low for the user 90. In this case, the user 90 should choose a new value in step S309. If the user 90 cannot finish the preset number of exercise movements, step S313 may be followed to calculate the maximum muscle strength.

For further accuracy, the muscle strength value generating condition may further include the moving distance of the drag unit 10 being greater than, equal to, or close to the preset shift value 37. In this case, the control unit 30 considers the exercise movement to be completed only when the user 90 moves the drag unit 10 from the start position to the final position.

In steps S301 to S308, the user 90 can set the start position and the final position of the drag unit 10 through the operation display unit 20 to set the preset shift value 37. Therefore, when the moving distance of the drag unit 10 is greater than, equal to, or close to the preset shift value 37, the control unit 30 considers the muscle test movement to be completed.

In summary, at least one exercise movement is used to calculate the average moving distance. The maximum muscle strength of the user 90 is then calculated (estimated) or directly measured by following steps S11 to S17. In another embodiment described by steps S21 to S30, different test resistance values are given based on different proportions of the assumed maximum muscle strength, and the resistance can be adjusted based on the performance of the user 90. In steps S11 to S17 and steps S21 to S30, the user 90 is given a chance to warm up before taking the maximum muscle strength test. This avoids or reduces the possibility of muscle injury for the user 90.

In steps S201 to S206 and steps S301 to S313, the moving distance is measured to ensure that the user 90 finishes the exercise completely, and therefore ensure an accurate strength measurement. For bodybuilding exercises, it is important to finish every movement completely, because this affects the performance in real contests. For example, completion of exercises such as bench press, deadlift, and squat is dependent on completion of the exercise movements. For example, for the squat exercise, the hips have to reach a point lower than the knee, so that the lifter bends his knees and drops into a squatting position with the hip crease (where the top of the leg meets the hip) below the top of the knee. Because everyone has their own distinct body and joint flexibility, it is necessary to record the full exercise movements for further tests, so that progress can be evaluated. The recording of the exercise movements and the evaluation of progress is important to build up performance, especially for bodybuilding, weight lifting, and other physical exercises.

While several preferred embodiments of the present invention have been described herein with reference to the figures, it is to be understood by those of ordinary skill in the art that various changes in form and detail may be made therein without departing from the spirit and scope of the present invention, which is set forth in the appended claims.

What is claimed is:

1. A maximum muscle strength measuring method, which is applicable to a user and a muscle training device, the muscle training device including a drag unit, an operation display unit, and a control unit, the method comprising the steps of:
    selecting a muscle of the user or a motion to be measured through the operation display unit;
    setting up a resistance value through the display unit and generating at least one test resistance value based on different proportions of the resistance value;
    generating at least one drag force based on the at least one test resistance value;
    overcoming the at least one drag force by the user moving or steadily holding the drag unit, and measuring a moving distance or a steady operation time of the drag unit for completing the motion by a position sensor and the control unit;
    judging whether the moving distance or the steady operation time of the drag unit meets a condition for generating a muscle strength value or not, wherein the condition for generating the muscle strength value includes the moving distance or the steady operation time of the drag unit;
    obtaining a maximum muscle strength coefficient based on an accumulative number of times that the user meets the condition for generating the muscle strength value continuously in the step e, and calculating the muscle strength value via dividing the resistance value by the maximum muscle strength coefficient;
    generating a test drag force, for the drag unit to exert or resist, based on the muscle strength value;
    lowering the muscle strength value by a lowering proportion when the user is unable to overcome the test drag force and meet the condition for generating the muscle strength value, and returning back to the step g;
    raising the muscle strength value by a raising proportion and returning back to the step g when the user continuously overcomes the test drag force to complete more than one time of the measurement and meets the condition for generating the muscle strength value; and
    outputting the muscle strength value as the maximum muscle strength when the user is able to overcome the test drag force and meet the condition for generating the muscle strength value only once.

2. The measuring method of claim 1, wherein the condition for generating the muscle strength value may be adjusted to a certain proportion of the moving distance or the steady operation time.

3. The measuring method of claim 1, wherein the condition for generating the muscle strength value based on the moving distance or the steady operation time is set or inputted through the operation display unit.

4. The measuring method of claim 1, wherein a start position and a final position or a start time and an end time for the condition for generating the muscle strength value are set or inputted through the operation display unit.

5. The measuring method of claim 1, wherein the condition for generating the muscle strength value is set and inputted into the operation display unit by means of a sound or motion sensor.

6. The measuring method of claim 1, wherein the moving distance or the steady operation time is an average moving distance or an average steady operation time where the user has overcome the drag force or the test drag force at least once to move the drag unit as in the step d.

7. A maximum muscle strength measuring method, which is applicable to a user and a muscle training device, the muscle training device including a drag unit, an operation display unit, and a control unit, the method comprising the steps of:
    selecting a muscle of the user or a motion to be measured through the operation display unit;
    setting up a resistance value through the operation display unit, and generating a test resistance value by the control unit, and generating a test drag force, for the drag unit to exert or resist, based on the test resistance value;
    overcoming the test drag force by the user moving or steadily holding the drag unit;
    judging whether a moving distance or a steady operation time of the drag unit meets the condition for generating a muscle strength value or not, wherein the condition for generating the muscle strength value is based on the moving distance or the steady operation time of the drag unit, and determining the moving distance and the steady operation time of the drag unit for completing a measurement by a position sensor and the control unit;
    counting an accumulative number of times of completing the measurement in the step d until a preset number of times is reached; and
    obtaining a maximum muscle strength coefficient based on the accumulative number of times, and calculating the maximum muscle strength by multiplying the resistance value by the maximum muscle strength coefficient.

8. The measuring method of claim 7, wherein the condition for generating the muscle strength value is adjusted to a certain proportion of the moving distance or the steadily operation time of the drag unit.

9. The measuring method of claim 7, wherein the condition for generating the muscle strength value based on the moving distance or the steady operation time are set or inputted through the operation display unit, and a start position and a final position or a start time and an end time of the moving distance or the steady operation time are set or inputted through the operation display unit.

10. The measuring method of claim 7, wherein the condition for generating the muscle strength value is set and inputted into the operation display unit by means of a sound or motion sensor.

* * * * *